US009777765B2

(12) United States Patent
Schilling et al.

(10) Patent No.: US 9,777,765 B2
(45) Date of Patent: Oct. 3, 2017

(54) FASTENING SYSTEM

(71) Applicant: OTTO BOCK HEALTHCARE GMBH, Duderstadt (DE)

(72) Inventors: Matthias Schilling, Weissenborn-Luderode (DE); David Hochmann, Berlin (DE)

(73) Assignee: OTTO BOCK HEALTHCARE GMBH, Duderstadt (DE)

( * ) Notice: Subject to any disclaimer, the term of this patent is extended or adjusted under 35 U.S.C. 154(b) by 0 days.

(21) Appl. No.: 14/779,549

(22) PCT Filed: Mar. 27, 2014

(86) PCT No.: PCT/EP2014/000828
§ 371 (c)(1),
(2) Date: Sep. 23, 2015

(87) PCT Pub. No.: WO2014/154359
PCT Pub. Date: Oct. 2, 2014

(65) Prior Publication Data
US 2016/0040710 A1  Feb. 11, 2016

(30) Foreign Application Priority Data
Mar. 28, 2013  (DE) .......................... 10 2013 005 366

(51) Int. Cl.
*A61F 2/00* (2006.01)
*A61F 5/01* (2006.01)
*F16C 11/04* (2006.01)

(52) U.S. Cl.
CPC ................ *F16C 11/04* (2013.01); *A61F 2/00* (2013.01); *A61F 5/01* (2013.01); *A61F 5/0102* (2013.01);
(Continued)

(58) Field of Classification Search
CPC .............. F16C 11/04; A61F 2220/0041; Y10T 24/44026; Y10T 16/54038
(Continued)

(56) References Cited

U.S. PATENT DOCUMENTS

| 3,732,861 A | 5/1973 | Lehneis |
| 4,428,094 A | 1/1984 | Emain |

(Continued)

FOREIGN PATENT DOCUMENTS

DE  202013000384 U1  5/2013

OTHER PUBLICATIONS

PCT International Search Report for PCT International Patent Application No. PCT/EP2014/000828, dated Jun. 2, 2014.

*Primary Examiner* — Robert J Sandy
(74) *Attorney, Agent, or Firm* — Holland & Hart LLP

(57) ABSTRACT

The present disclosure relates to a fastening system for fastening a first component on a second component, wherein the first component has a first bearing surface and a first direction of extent, and the second component has a second bearing surface and a second direction of extent, and an included angle between the first direction of extent and the second direction of extent is adjustable steplessly within an angle range. The fastening system has a clamp element with which the first component can be fastened on the second component when the first bearing surface lies on the second bearing surface, and, in the fastened state of the two components, at least one force-transmitting element is clamped between the two bearing surfaces.

19 Claims, 2 Drawing Sheets

(52) U.S. Cl.
CPC ............ *A61F 5/013* (2013.01); *A61F 5/0123* (2013.01); *A61F 5/0127* (2013.01); *A61F 2220/0041* (2013.01); *Y10T 16/5403* (2015.01); *Y10T 16/54038* (2015.01); *Y10T 24/44026* (2015.01)

(58) Field of Classification Search
USPC .................................................. 16/221–392
See application file for complete search history.

(56) References Cited

U.S. PATENT DOCUMENTS

| | | | |
|---|---|---|---|
| 6,902,200 B1 * | 6/2005 | Beadle | F16C 11/04 285/185 |
| 7,081,102 B1 | 7/2006 | Koetter et al. | |
| 7,896,568 B2 * | 3/2011 | Atkinson | E05D 5/125 248/160 |
| 8,142,381 B1 | 3/2012 | Birnbaum | |
| 2013/0053741 A1 | 2/2013 | Pittaccio et al. | |

\* cited by examiner

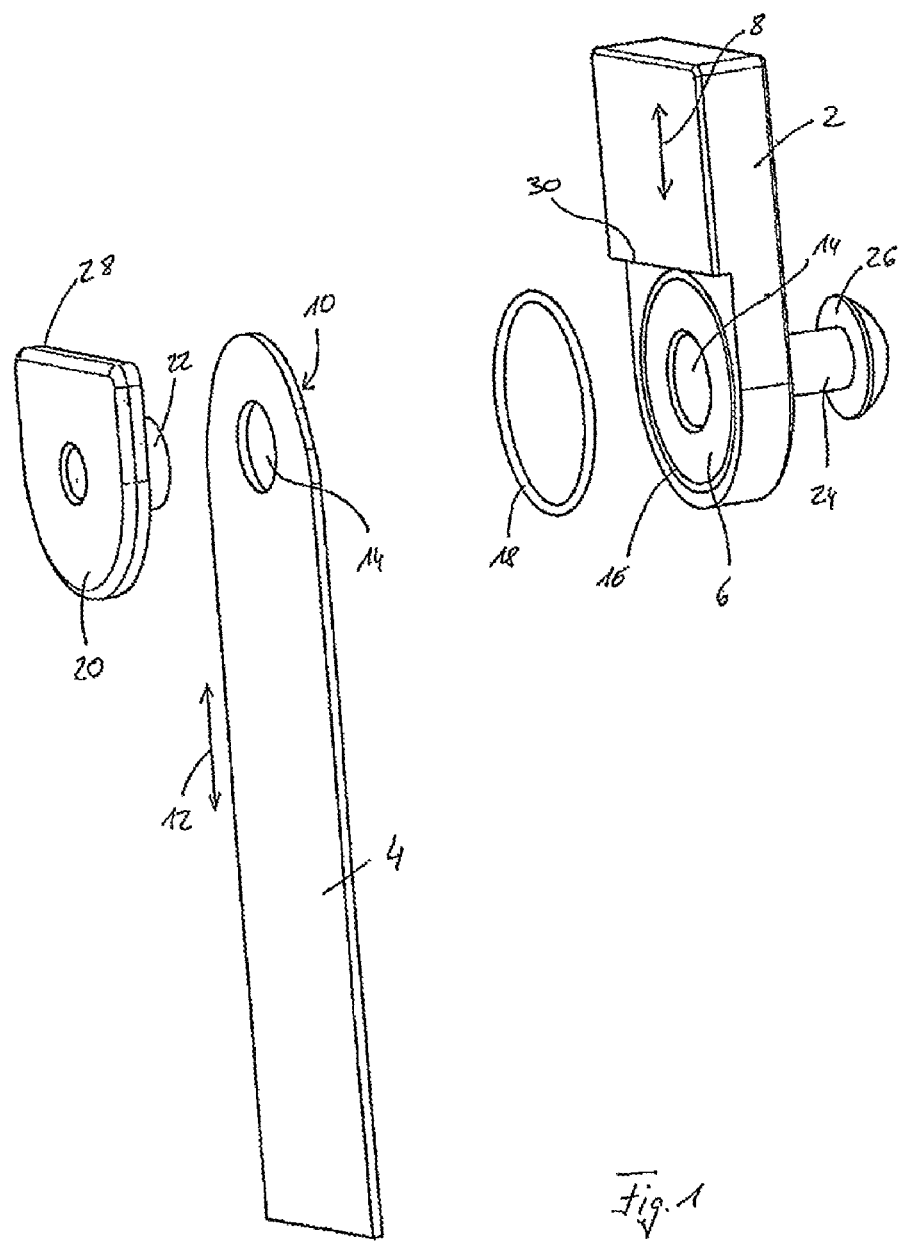

ND OF PAGE# FASTENING SYSTEM

TECHNICAL FIELD

The invention relates to a fastening system for fastening a first component to a second component, wherein the first component has a first bearing surface and a first direction of extent, and the second component has a second bearing surface and a second direction of extent, and an included angle between the first direction of extent and the second direction of extent is adjustable steplessly within an angle range.

BACKGROUND

Fastening systems of this kind have long been known from the prior art. They are used, for example, in orthopedic devices such as orthoses and prostheses, in order to adapt the respective device to the individual physical circumstances presented by the subsequent wearer of the orthosis or prosthesis. For example, in leg and ankle orthoses, a rail system is often used comprising joints between which the individual rails are located. The individual adaptation is carried out not only by modifying the length of the rails present between the individual joints but also, for example, by changing the position of, for example, the ankle joint in a load-free neutral position. It is therefore important to be able to arrange the two components at an individually adjustable angle to each other. Particularly in the use as an ankle orthosis, but also in other possible uses, this connection between the two components is subjected to considerable mechanical loads, particularly on account of the substantial torques that occur. However, once the two components have been connected to each other, they should not move relative to each other during normal use of the respective device and, in particular, they should not change the included angle. The connection must therefore be designed to be stable.

It is known from the prior art that the two components to be connected to each other can be configured such that they bear on each other along a side surface. If, for example, an orthosis is now adapted to the individual requirements of the person wearing it, the angle at which this side surface extends relative to one of the components is altered by a specific cutting of the respective component, such that the outer contour of the respective component now serves as an abutment for this included angle. This has several disadvantages. First, structural modifications to one component are needed in order to achieve an optimal adaptation. Second, it is possible only to a very limited extent to compensate for incorrect machining, so that in such an event the component has to be discarded and replaced by another new component, which has to be subjected anew to the additional machining. Particularly when the chosen fit and the chosen included angle prove not to be the optimal choices, it is often impossible to make simple changes to these settings.

However, in the fastening systems from the prior art, the chosen contour of the abutment is necessary in order to be able to withstand the mechanical loads that arise.

As an alternative to this, a stepwise adjustment of the chosen included angle is also known, wherein the two components to be fastened to each other can, for example, be screwed, riveted or pinned. Although a subsequent change is possible here, particularly if the two components have been screwed together, a stepless adjustability of the included angle is not provided. However, stepless adjustability is often necessary in order to be able to achieve the optimal setting for each wearer of the orthosis or prosthesis.

SUMMARY

The problem addressed by the invention is therefore that of improving a fastening system in such a way that, despite having a small overall size, it permits a stepless adjustment of the included angle, is able to take up the expected mechanical forces and yet allows the two components to be fastened to each other in such a way that they are easily releasable.

The invention solves the stated problem by virtue of a fastening system as per the preamble of claim 1, characterized in that the fastening system has a clamp element with which the first component can be fastened to the second component when the first bearing surface lies on the second bearing surface, and in that, in the fastened state of the two components, at least one force-transmitting element is clamped between the two bearing surfaces. It is also possible to use precisely one force-transmitting element. On the one hand, with this design of the fastening system, the clamp element permits an easily releasable connection between the two components. On the other hand, the force-transmitting element additionally ensures that the clamped fastening, which would otherwise be too weak, is able to withstand the mechanical loads that occur. This is not the case in conventional clamping with screws, such that the use of a clamp element on its own would not be suitable for designing the corresponding fastening system for the mechanical loads.

By means of the fastening system according to the invention, the first component and the second component are fastened to each other and secured such that a movement of the two components relative to each other is no longer possible under the forces that are expected to occur. These forces that are expected to occur do of course depend on the use for which the components are intended. For example, if two components of an ankle orthosis are connected to each other, much greater forces occur during normal use than is the case, for example, with an arm orthosis. Accordingly, the respective bearing surfaces and/or the force-transmitting element must be designed to be able to withstand the expected mechanical loads.

The force-transmitting element preferably has a closed contour. The force-transmitting element is particularly advantageously an O-ring.

If the first component is now to be fastened to the second component, for example if an orthosis or prosthesis is intended to be adapted individually to the body of the wearer, the first bearing surface and the second bearing surface are placed onto each other. In this state, a movement and in particular a pivoting of the two components relative to each other is possible, such that the included angle between the two directions of extent of the two components can be adjusted steplessly. When a desired included angle is reached, the clamp element is tightened and the two components are connected to each other. In the case where a fastening system of this kind is used without a force-transmitting element, the clamping force applied by the clamp element, and therefore the static friction between the two bearing surfaces, determines whether the fastening system withstands an applied force or a torque or whether the two components move or pivot relative to each other. However, the actual force flow between the two contact surfaces bearing on each other is not homogeneous across the entire surface area of the bearing surface and instead, on account of surface roughnesses, is intensified in some areas and weakened in other areas. The position and extent of these areas cannot be controlled by production engineering, and therefore an estimation of the maximum adherence is not possible.

It is only by using a force-transmitting element between the two bearing surfaces that it is possible to obtain a reproducible and predefinable profile of the force flow. It has been found here that the adherence between the force-transmitting element and the two bearing surfaces can be maximized by the closed contour of the force-transmitting element. By suitable choice of the geometric shape and/or of the material from which the force-transmitting element is made, it is possible to influence and optimize the adherence and therefore the mechanical stability of the fastening of the two components to each other.

The direction of extent of the respective component can be, for example, the direction of a side surface or the direction of greatest extent of the respective component. This is irrelevant as regards the function of the fastening system, since the important point is simply that, once the directions of extent have been chosen, the included angle between these two directions is adjustable steplessly within an angle range. The size of the angle range is not influenced here by the choice of the directions of extent, whereas the absolute values of the respective included angle can of course depend on this choice.

Advantageously, the angle range lies in a plane which is defined by the first bearing surface. A change of the included angle thus signifies a pivoting of the two components relative to each other about a pivot axis that lies perpendicularly to the first bearing surface.

The clamp element preferably extends through a bore in the first bearing surface and the second bearing surface. This has the effect, on the one hand, that the fastening system can be made particularly small and, on the other hand, that the two bores in the first bearing surface and in the second bearing surface have to be brought into coincidence with each other in order to fasten the two components to each other, which permits a particularly simple orientation of the two components relative to each other.

Advantageously, the clamp element therefore has a threaded plate, which can be positioned on a side of the component opposite the respective bearing surface. A screw, for example, engages in this threaded plate, extends through the two bores in the first bearing surface and in the second bearing surface and thus through the two components and, for example, lies with a screw head or a washer on the outlet side of the respective component. If the screw is now tightened, a clamping force is applied such that the force-transmitting element is clamped between the two components or their bearing surfaces, resulting in a force flow that is well defined and reproducible. To adjust the included angle between the two directions of extent of the two components, it is sufficient in this case to slightly loosen the screw and thus reduce the clamping force, such that a pivoting of the two components relative to each other becomes possible. The pivot axis in this case advantageously extends centrally through the clamp element, which extends through the bores in the two components and in the two bearing surfaces. In this case, the clamp element is composed of the threaded plate and of the screw. Alternative clamp elements comprise a screw and a nut and, if appropriate, a washer. Of course, it is also possible to conceive of other clamp connections that may be advantageous for other fields of use.

The clamp element, in particular the threaded plate, preferably has at least one stop which, in the fastened state, lies on at least one counter-stop on one of the components. Thus, in addition to the applied clamping force and to the adherence acting between the bearing surfaces and the force-transmitting element, it is ensured that a pivoting of the two components relative to each other is made difficult in the state in which they are fastened to each other. A fastening system is thereby obtained that withstands even greater mechanical loads and that can thus be used in a wide range of applications.

Preferably, the clamp element extends through the force-transmitting element in the fastened state of the two components. The force-transmitting element has a closed contour and is therefore ring-shaped. The use of an O-ring has proven particularly advantageous. The clamp element also extends through this ring.

The force-transmitting element is advantageously made of an elastic material, for example rubber. This has the effect that the force-transmitting element is deformed when clamped between the two bearing surfaces and, in this way, the static friction between the two bearing surfaces and the force-transmitting element is maximized. Moreover, in this embodiment, the force-transmitting element is able to follow any irregularities and surface roughnesses, for example, and can thus contribute about its entire circumference to the transmission of the retaining force.

In a particularly preferred embodiment of the present invention, a groove is arranged in the first bearing surface and/or the second bearing surface, into which groove the force-transmitting element can be fitted. This prevents the force-transmitting element from slipping or moving out of place while the two components are being fastened to each other. Moreover, the force-transmitting element can be secured in the groove, for example by being glued therein. This ensures that the force-transmitting element is not lost, for example during transportation. A person using the fastening system therefore always receives a functional system, without any risk of the force-transmitting element, necessary for the functioning of the system, being lost. This groove preferably extends as far away as possible from the bore through which the clamp element extends. This has the effect, on the one hand, that torques are applied as far away as possible from the potential pivot axis and, on the other hand, that it is possible to use a force-transmitting element that is as large as possible. As a result of the increased static friction between the force-transmitting element and the respective bearing surface, as large as possible a contact area between these components is advantageous for the stability of the fastening.

As has already been mentioned, the first component and the second component are advantageously part of an orthopedic device, in particular a prosthesis or orthosis. The orthopedic device is preferably a joint.

In the present invention, the fastening system does not have to be designed as a separate component and instead contains special configurations of the first component and of the second component. These include, for example, the two bearing surfaces, which should be designed such that they are able to lie completely on each other. For example, in the case of an ankle orthosis, an ankle joint is used at whose distal end a foot assembly is arranged that serves to support the foot. The angle at which these two components, i.e. the foot assembly and the joint, are arranged on each other has to be matched to the respective individual characteristics of the wearer. To be able to use a fastening system according to the invention in this case, the first component, which in this case is formed by the joint for example, and the second component, which is formed by the foot assembly, should have the two bearing surfaces. An additional intermediate component, connected on the one hand to the first component and on the other hand to the second component in a different way, is thus safely avoided, such that a particularly simple, cost-effective, rapid and reliable fastening is possible.

If one of the two components is a part of a joint, for example one of the pivotable branches of a joint, the pivotability of the joint is not impaired by the fastening of the two components to each other. For example, if the joint has two branches pivotable relative to each other, the second component for example is formed only by one of these two branches. A first component, for example a rail or a similar element, is arranged on this second component. A rigid fastening of the rail to the branch of the joint is thus achieved, without adversely affecting the pivotability of the two branches of the joint relative to each other. A fastening system according to an illustrative embodiment of the present invention is advantageous wherever two components are intended to be fastened at a certain angle and in a certain position relative to each other such that, in this state, they can no longer be moved relative to each other under the forces that are to be expected. The actually selected angle or the actual position can be individually adjusted. This is advantageous not only in orthoses and prostheses but also, for example, for individual adaptation of wheelchairs or similar aids.

BRIEF DESCRIPTION OF THE DRAWINGS

An illustrative embodiment of the present invention is explained in more detail below with reference to a drawing, in which FIG. 1 shows a fastening system according to a first illustrative embodiment of the present invention in an exploded view.

DETAILED DESCRIPTION

Figure 4:
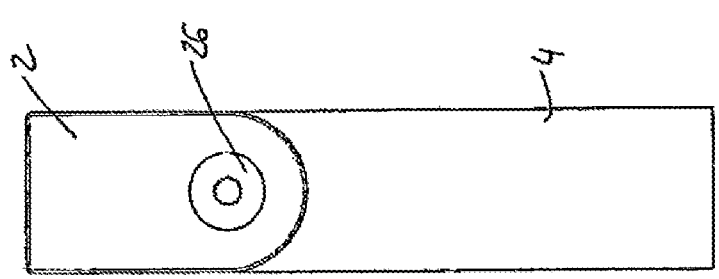
FIGS. 2 to 4 show different views of the fastening system from FIG. 1 in the assembled state.

FIG. 1 shows a fastening system with a first component 2 and a second component 4. The first component 2 has a first bearing surface 6 and a first direction of extent 8. The second component 4 has a second bearing surface 10 and a second direction of extent 12. The first component 2 and the second component 4 each have a bore 14, which also extends through the respective bearing surface 6, 10. To fasten the first component 2 and the second component 4 to each other, the two bores 14 are placed in coincidence with each other.

In the first bearing surface 6 there is a groove 16 into which is inserted a force-transmitting element 18, which is designed as an O-ring in the illustrative embodiment shown.

The fastening system has a clamp element composed of a threaded plate 20, which has a projection 22 in which the thread is located, and has a screw 24. To fasten the two components 2, 4 to each other, the screw 24 is screwed through the two bores 14 into the projection 22. A screw head 26 comes to bear on the first component 2, while the threaded plate 20 bears on the second component 4. By means of the screw 24 and the threaded plate 20, a clamping force is exerted on the two components 2, 4 and in particular on the force-transmitting element 18.

The threaded plate 20 shown in FIG. 1 has a stop 28 which, in the connected state, cooperates with a counter-stop 30 arranged on the first component 2.

Figure 3:
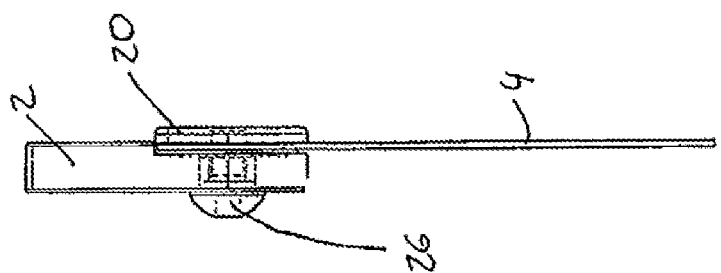
Figure 2:
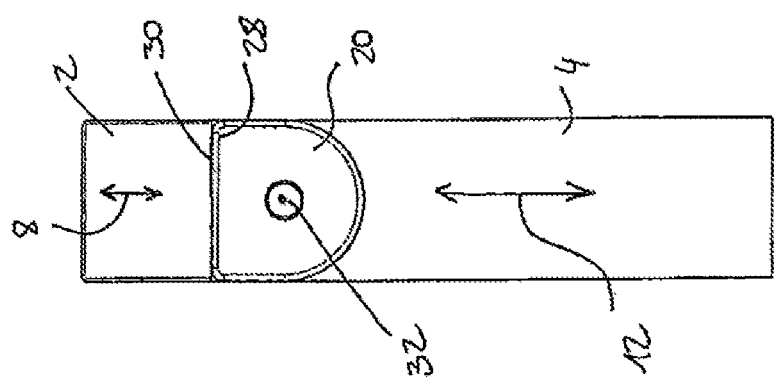

In FIGS. 2 to 4, the fastening system shown in FIG. 1 can be seen from different views in the assembled state. FIG. 2 shows the first component 2 and the second component 4, and also the threaded plate 20 which bears with the stop 28 on the counter-stop 30. It will be seen that the two directions of extent 8, 12 run parallel to each other, such that the included angle in this case is 180 degrees. By simple loosening of the clamp element, i.e. in particular of the screw 24 in the projection 22 of the threaded plate 20, the clamping force is reduced, and the first component 2 and the second component 4 can therefore be pivoted relative to each other. Here, a pivot axis 32 in FIG. 2 runs out from the plane of the drawing centrally through the two bores 14 and the clamp element composed of screw 24 and threaded plate 22. The second component 4 not only pivots relative to the first component 2 but also relative to the threaded plate 20, such that the stop 28 bears on the counter-stop 30 independently of the included angle, and further pivoting is thus prevented in the fastened state.

FIG. 3 shows the fastening system in a side view. The first component 2 and the second component 4 are clamped by the threaded plate 20 and the screw 24 with the screw head 26.

FIG. 4 shows the fastening system in a rear view, such that only the first component 2, the second component 4 and the screw head 26 can be seen.

LIST OF REFERENCE SIGNS 2 first component
4 second component
6 first bearing surface
8 first direction of extent
10 second bearing surface
12 second direction of extent
14 bore
16 groove
18 force-transmitting element
20 threaded plate
22 projection
24 screw
26 screw head
28 stop
30 counter-stop
32 pivot axis

The invention claimed is:
1. A fastening system, comprising:
a first component having a first bearing surface and a first direction of extent;
a second component having a second bearing surface and a second direction of extent, the second bearing surface lying on the first bearing surface, wherein an included angle between the first direction of extent and the second direction of extent is adjustable steplessly within an angle range;
a clamp assembly with which the first component is fastened to the second component when the first bearing surface lies on the second bearing surface;
at least one force-transmitting member clamped between the first and second bearing surfaces when the first and second components are fastened to each other;
wherein the first component and the second component are part of an orthopedic device.
2. The fastening system as claimed in claim 1, wherein the force-transmitting member has a closed contour and is configured as an O-ring.

3. The fastening system as claimed in claim 1, wherein the angle range lies in a plane which is defined by the first bearing surface.

4. The fastening system as claimed in claim 1, wherein the clamp assembly includes a first member that extends through a bore in the first bearing surface and the second bearing surface.

5. The fastening system as claimed in claim 1, wherein the clamp assembly includes a threaded plate, which is positionable on a side of one of the first and second components opposite a respective one of the first and second bearing surfaces.

6. The fastening system as claimed in claim 5, wherein the clamp assembly includes at least one stop which, when the clamp is in a fastened state, lies on at least one counter-stop on one of the first and second components.

7. The fastening system as claimed in claim 4, wherein the clamp assembly includes a first member that extends through the force-transmitting element when the first and second components are fastened to each other.

8. The fastening system as claimed in claim 1, wherein the force-transmitting member comprises an elastic material.

9. The fastening system as claimed in claim 1, wherein a groove for receiving the force-transmitting member is arranged in one of the first bearing surface and the second bearing surface.

10. The fastening system as claimed in claim 1, wherein the orthopedic device is a joint.

11. A fastening system, comprising:
a first component having a first bearing surface;
a second component having a second bearing surface, the second bearing surface contacting the first bearing surface, the first and second components being adjustable within an angle range relative to each other;
a clamp assembly configured to fasten the first component to the second component when the first bearing surface contacts the second bearing surface;
at least one force-transmitting member positioned between the first and second bearing surfaces when the first and second components are fastened to each other;
wherein the first component and the second component are part of an orthopedic device.

12. The fastening system as claimed in claim 11, wherein the force-transmitting member has a closed contour.

13. The fastening system as claimed in claim 11, wherein the angle range is measured within in a plane defined by the first bearing surface.

14. The fastening system as claimed in claim 11, wherein the clamp assembly includes a first member that extends through a bore formed in the first bearing surface and the second bearing surface.

15. The fastening system as claimed in claim 11, wherein the clamp assembly includes a threaded plate, which is positionable on a side of one of the first and second components opposite a respective one of the first and second bearing surfaces.

16. The fastening system as claimed in claim 11, wherein the clamp assembly includes at least one stop which, when the clamps is in a fastened state, lies on at least one counter-stop on one of the first and second components.

17. The fastening system as claimed in claim 11, wherein the clamp assembly includes a first member that extends through the force-transmitting member when the first and second components are fastened to each other.

18. The fastening system as claimed in claim 11, wherein the force-transmitting member comprises an elastic material.

19. The fastening system as claimed in claim 11, wherein a groove to receive the force-transmitting member is arranged in one of the first bearing surface and the second bearing surface.

* * * * *